(12) United States Patent
Lesage et al.

(10) Patent No.: US 11,013,634 B2
(45) Date of Patent: May 25, 2021

(54) CRYOGENIC COMPOSITION

(71) Applicants: Patrick Lesage, Saint Malo (FR);
Alexandre Lesage, Rennes (FR)

(72) Inventors: Patrick Lesage, Saint Malo (FR);
Alexandre Lesage, Rennes (FR)

( * ) Notice: Subject to any disclaimer, the term of this patent is extended or adjusted under 35 U.S.C. 154(b) by 215 days.

(21) Appl. No.: 16/070,465

(22) PCT Filed: Jan. 19, 2017

(86) PCT No.: PCT/FR2017/050113
§ 371 (c)(1),
(2) Date: Jul. 16, 2018

(87) PCT Pub. No.: WO2017/125687
PCT Pub. Date: Jul. 27, 2017

(65) Prior Publication Data
US 2019/0076292 A1 Mar. 14, 2019

(30) Foreign Application Priority Data

Jan. 20, 2016 (FR) .................................. 1650448

(51) Int. Cl.
*A61F 7/00* (2006.01)
*F25D 3/08* (2006.01)
*C09K 5/06* (2006.01)
*A61F 7/02* (2006.01)

(52) U.S. Cl.
CPC .................. *A61F 7/00* (2013.01); *A61F 7/02* (2013.01); *C09K 5/06* (2013.01); *F25D 3/08* (2013.01); *A61F 2007/0098* (2013.01); *A61F 2007/026* (2013.01); *A61F 2007/0214* (2013.01); *A61F 2007/0215* (2013.01); *A61F 2007/0219* (2013.01); *A61F 2007/0292* (2013.01); *F25D 2303/085* (2013.01)

(58) Field of Classification Search
CPC ...... A61F 2007/0098; A61F 2007/0214; A61F 2007/0215; A61F 2007/0219; A61F 2007/026; A61F 2007/0292; A61F 7/00; A61F 7/02; C09K 5/06; F25D 2303/085; F25D 3/08
See application file for complete search history.

(56) References Cited

U.S. PATENT DOCUMENTS 5,513,629 A 5/1996 Johnson
6,379,582 B1 4/2002 Putman
5,800,491 A1 10/2004 Ringleben et al.
(Continued)

OTHER PUBLICATIONS

International Search Report issued in International Application No. PCT/FR2017/050113 dated Apr. 20, 2017 (7 pages).
(Continued)

*Primary Examiner* — Yan Lan
(74) *Attorney, Agent, or Firm* — Hamre, Schumann, Mueller & Larson, P.C.

(57) ABSTRACT

The present invention relates to a novel cryogenic composition intended to be used in thermal treatment devices, and also to its process of preparation. The invention also relates to a thermal treatment device and more particularly to a medical device used to cool a part of the human or animal body, in particular after trauma, inflammation or a surgical act. The invention has application in the therapeutic and/or medical field but also in other fields, such as, for example, for the cooling or the maintenance at low temperature of foodstuffs.

14 Claims, 2 Drawing Sheets

(56) References Cited

U.S. PATENT DOCUMENTS

2002/0042641 A1  4/2002  Johnson
2009/0005842 A1  1/2009  Lin
2011/0024674 A1  2/2011  Copelli Yañez

OTHER PUBLICATIONS

Written Opinion issued in International Application No. PCT/FR2017/050113 dated Apr. 20, 2017 (5 pages).

CRYOGENIC COMPOSITION

BACKGROUND

The present invention relates to a novel cryogenic composition intended to be used in thermal treatment devices, and also to its process of preparation. The invention also relates to a thermal treatment device and more particularly to a medical device used to cool a part of the human or animal body, in particular after trauma, inflammation or a surgical act. The invention thus has application in the therapeutic and/or medical field but also in other fields, such as, for example, for the cooling or the maintenance at low temperature of foodstuffs.

Cryotherapy or cold treatment first appeared in the 1970s and is today widely used in the medical field for healing damaged tissues, promoting the closing up of wounds and relieving body pain, such as sprains, tendinitis or muscle strains. The concept thereof consists in exposing a portion of the human or animal body to cold, in order to cause it to secrete endorphins, which has the effect of bringing about analgesia and thus a lowering of the pain threshold. Cryotherapy is thus used after post-traumatic or post-surgical acts, for its hemolytic and anti-edematous action.

Cryotherapy uses different sources of cold:
- Nitrogen-based devices originating from the instantaneous gasification of liquid nitrogen, this technique involving the use of cumbersome and bulky equipment which is consequently difficult to handle.
- Water-based thermal treatment devices. Water is one of the materials which restores cold the most. However, at a temperature of less than 0° C., water is converted into ice and exhibits certain Disadvantages as a result of its solid structure, which is difficult to conform to an anatomical structure, and the very low temperature of which causes tissue injuries.
- Devices based on antifreeze compositions not exhibiting a phase change during freezing to −25° C. These compositions, present in the form of beads or gel, restore a very unstable cold which does not make possible effective use in cryotherapy. The devices using these compositions exhibit, during thawing, a surface temperature which can be of the order of −5° C. for gels to 10° C. for beads.
- Phase-change devices, such as those described in the patent EP 1 011 558. This patent describes compositions comprising water, an absorbent product of acrylic polymer type and a humectant. During freezing, a portion of the water present in the network of the absorbent product is released and changes phase in order to be converted into ice crystals. During warming, the water returns to the absorbent network. These compositions remain flexible and conformable. However, they are not very resistant to repeated freezing/thawing cycles and have a tendency to become less and less flexible as the cycles proceed, which renders them uncomfortable and less effective in use. These compositions additionally exhibit the disadvantage of requiring a container comprising a semipermeable region which is leaktight to water and permeable to air, which complicates the device. The latter also exhibits, during thawing, a surface temperature of less than 0° C. over a lengthy period, which accordingly reduces the duration of use of the device as it is advisable to wait for the temperature to stabilize above 0° C. or to insert an insulating layer between the device and the skin in order to use it.

SUMMARY OF THE INVENTION

In this context, the purpose of the present invention is to overcome the disadvantages of the devices of the prior art by providing a novel flexible and leaktight thermal treatment device which remains perfectly flexible after freezing and which does not rapidly deteriorate during the freezing/thawing cycles. The device of the invention exhibits the advantage of being able to be reused several times (up to approximately thirty times). A few minutes after it has thawed, the device of the invention exhibits a surface temperature slightly greater than 0° C. This temperature, ideally between 3° C. and 5° C., remains stable over a period of time of at least 60 minutes and which can range up to 120 minutes.

The Inventors have discovered that it is possible to achieve these performance qualities by using a cryogenic composition based on superabsorbent polymer, on water and on humectant, incorporated in a hydrophobic compound. They have observed that the hydrophobic compound creates a hydrophobic film or "insulating layer" around the polymer granules, thus trapping a portion of the water within them. This property confers a very high flexibility to the cryogenic composition.

DETAILED DESCRIPTION

Figure 1:
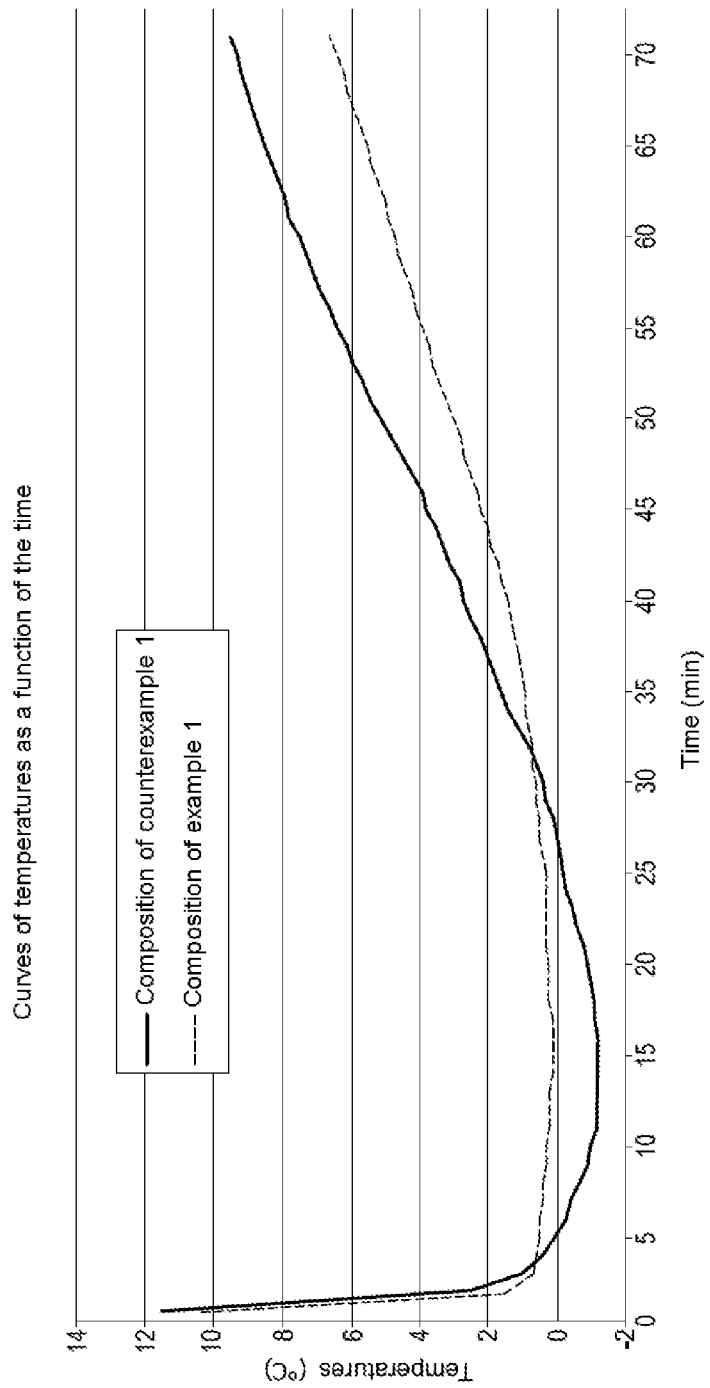
FIGS. 1 and 2 (FIGS. 1 and 2) represent curves of temperatures as a function of the time which are obtained for the cryogenic composition of example 1 compared to the cryogenic composition of counterexample 1, and obtained for the cryogenic composition of example 2 compared to the cryogenic composition of counterexample 1. The temperature of the sample is measured each minute for 70 minutes under a compression of 14 g.cm$^{-2}$, using a Testo 175 T2 temperature recorder, with a probe of NTC type. The measurements are carried out every minute at the interface between the frozen bag and a bag of water at 20° C. with a thickness of 2 cm.

Thus, according to a first aspect, a subject matter of the present invention is a cryogenic composition comprising a hydrophobic compound (a) in the liquid form in which granules of superabsorbent polymer (b) charged with water (c) and with humectant (d) are immersed, said hydrophobic compound (a) having a freezing point of less than 0° C.

The hydrophobic compound (a) capable of being used in the context of the invention advantageously exhibits a freezing point of less than −7° C., preferably of less than −10° C. and more preferably still of less than −15° C. Particularly preferably, the hydrophobic compound (a) exhibits a freezing point of less than −20° C. It advantageously exhibits a high molecular weight, ranging from 200 to 700 g·mol$^{-1}$. Mention may be made, among the preferred hydrophobic compounds (a), of neopentylene glycol diheptanoate, isopropyl sebacate, isodecyl neopentanoate, isostearyl isostearate, vaseline oil and their mixtures, and preferably neopentylene glycol diheptanoate, isopropyl sebacate, isodecyl neopentanoate, isostearyl isostearate and their mixtures. These products are sold, for example, by Stéarinerie Dubois under the references DUB DNPG (neopentylene glycol diheptanoate, freezing point: −55° C.), DUB DIS (isopropyl sebacate, freezing point: −20° C.), DUB VCI 10 (isodecyl neopentanoate, freezing point: −35° C.) or DUB ISIS (isostearyl isostearate) or by Interchimie under the name Huile de Vaseline Codex 22 (freezing point: −10° C.).

The hydrophobic compound (a) preferably represents from 0.2% to 3% by weight and more preferably still from 0.2% to 2%, with respect to the total weight of the cryogenic composition.

"Superabsorbent polymer" is understood to mean a polymer which is capable, in its dry state, of spontaneously absorbing at least 20 times its own weight of aqueous fluid, in particular of water. This polymer has a high capacity for absorbing and retaining water and aqueous fluids. After absorbing the aqueous liquid, the polymer particles, thus impregnated with aqueous fluid, remain insoluble in the aqueous fluid and thus retain their individual particulate state. Examples of superabsorbent polymers are described in the work "Absorbent polymer technology, Studies in polymer science 8" by L. Brannon-Pappas and R. Harland, published by Elsevier, 1990.

Mention may be made, among the superabsorbent polymers (b) capable of being used in the context of the present invention, of crosslinked sodium or potassium polyacrylates, polyacrylamides, copolymers based on ethylene and maleic anhydride, vinyl alcohol copolymers, crosslinked polyethylene oxide, polymers based on starch, on gum and on cellulose derivatives, pectins, alginates, agar (or agarose), polyethyleneamines, polyvinylamines and their mixtures. The superabsorbent polymer (b) is preferably a crosslinked acrylic homo- or copolymer and more preferably still a crosslinked potassium acrylic homo- or copolymer.

The superabsorbent polymer (b) is generally used in an amount ranging from 1% to 6% by weight and preferably from 1.5% to 3%, with respect to the total weight of the cryogenic composition.

Advantageously, the granules of superabsorbent polymer (b) of the invention are provided in the form of spherical particles having a diameter of 1 to 6 mm when they are dehydrated. According to an even more preferred embodiment, the spherical particles of superabsorbent polymer (b) are sodium or potassium polyacrylate beads and more preferably still potassium polyacrylate beads preferably having a diameter of 1 to 3 mm, when they are dehydrated. Said spherical particles can absorb more than 40 times their weight, this characteristic being defined under standard temperature (25° C.) and pressure (100 000 Pa) conditions and for water. Once hydrated, the spherical particles of superabsorbent polymer (b) swell and form soft beads.

The humectant (d) of the invention can be chosen from glycerol, sorbitol, polyethylene glycol, (di)propylene glycol, polypropylene glycol, 1,5-pentanediol, propylene glycol, butylene glycol, diethylene glycol, liquid paraffin and their mixtures, preferably from glycerol, (di)propylene glycol, polypropylene glycol and their mixtures and more preferably still from (di)propylene glycol, polypropylene glycol and their mixtures. Dipropylene glycol is the most preferred humectant (d).

The humectant (d) is generally used in an amount ranging from 6% to 10% by weight and preferably from 7% to 9%, with respect to the total weight of the cryogenic composition.

According to a preferred embodiment, the cryogenic composition of the invention comprises:

(a) from 0.2% to 3% and preferably from 0.2% to 2% by weight of a hydrophobic compound, the freezing point of which is less than 0° C., (b) from 1% to 6% and preferably from 1.5% to 3% by weight of superabsorbent polymer granules, (c) from 75% to 95% and preferably from 85% to 90% by weight of water, (d) from 6% to 10% and preferably from 7% to 9% by weight of a humectant, said percentages being expressed as percentages by weight with respect to the total weight of the composition, and the total weight of the composition representing 100%.

Another subject matter is a process for the preparation of a cryogenic composition according to the invention, comprising the following steps:

(i) mixing the water (c) and the humectant (d), under stirring, (ii) adding the granules of superabsorbent polymer (b) to the mixture obtained at the end of step (i), under stirring, (iii) maturing the granules of superabsorbent polymer (b) present within the mixture obtained at the end of step (ii), by allowing said mixture to stand at room temperature, preferably until the granules of superabsorbent polymer (b) have reached a size of between two and four times their initial size, (iv) incorporating the mixture obtained at the end of step (iii) in a container comprising the hydrophobic compound (a) in the liquid form, under stirring, in order to create a hydrophobic film or "insulating layer" around the granules of superabsorbent polymer (b).

Step (iii) of maturing the granules of superabsorbent polymer (b) is preferably carried out over a period of time ranging from 1 to 5 hours and more preferably still over a period of time ranging from 2 to 4 hours.

A thermal treatment device comprising a leaktight container, within which is contained the present cryogenic composition, also forms part of the invention. The container is advantageously made of a flexible material, such as polyvinyl chloride (PVC), polychloroprene (neoprene), polytetrafluoroethylene (PTFE) or polyethylene (PE), and preferably of polyvinyl chloride (PVC). The device is preferably a leaktight and flexible medical bag which can be applied to a part of the human or animal body, for example in order to resorb hematomas or edemas or to ease pain.

The invention is thus mainly targeted at medical devices chosen from a face mask, a splint for the shoulder, elbow, ankle, knee, hip or wrist, and any support comprising a leaktight and flexible medical bag according to the invention.

The cryogenic composition according to the invention, or the thermal treatment device according to the invention, can be used to cool a part of the human or animal body, preferably after trauma, inflammation or a surgical act. The temperature can be monitored visually using a thermochromic pigment, added beforehand to the cryogenic composition of the invention. It can also be present in the constituent material containing it. This pigment can be a thermochromic pigment, such as those sold by OliKrom.

The thermal treatment device of the invention can also be intended for non-medical applications and be used to lower or maintain the temperature of foodstuffs, or to promote their preservation, or for the transportation in cold environment of heat-sensitive articles. In this case, the temperature can be monitored visually using a thermochromic pigment as described above.

The thermal treatment device of the invention can be used in a thermal treatment process, preferably in a process for the thermal treatment of a part of the human or animal body, comprising the following steps:

(i') freezing a device according to the invention to a temperature of less than 0° C. and preferably to a temperature of between −20° C. and −30° C., over a period of time which can range from 2 to 4 hours, (ii') manual kneading of the device obtained at the end of step (i'), (iii') application of the device obtained at the end of step (ii') to a part of the human or animal body, using or not using a medical device according to the invention, preferably over a period of time of between 30 minutes and 120 minutes.

Figure 2:
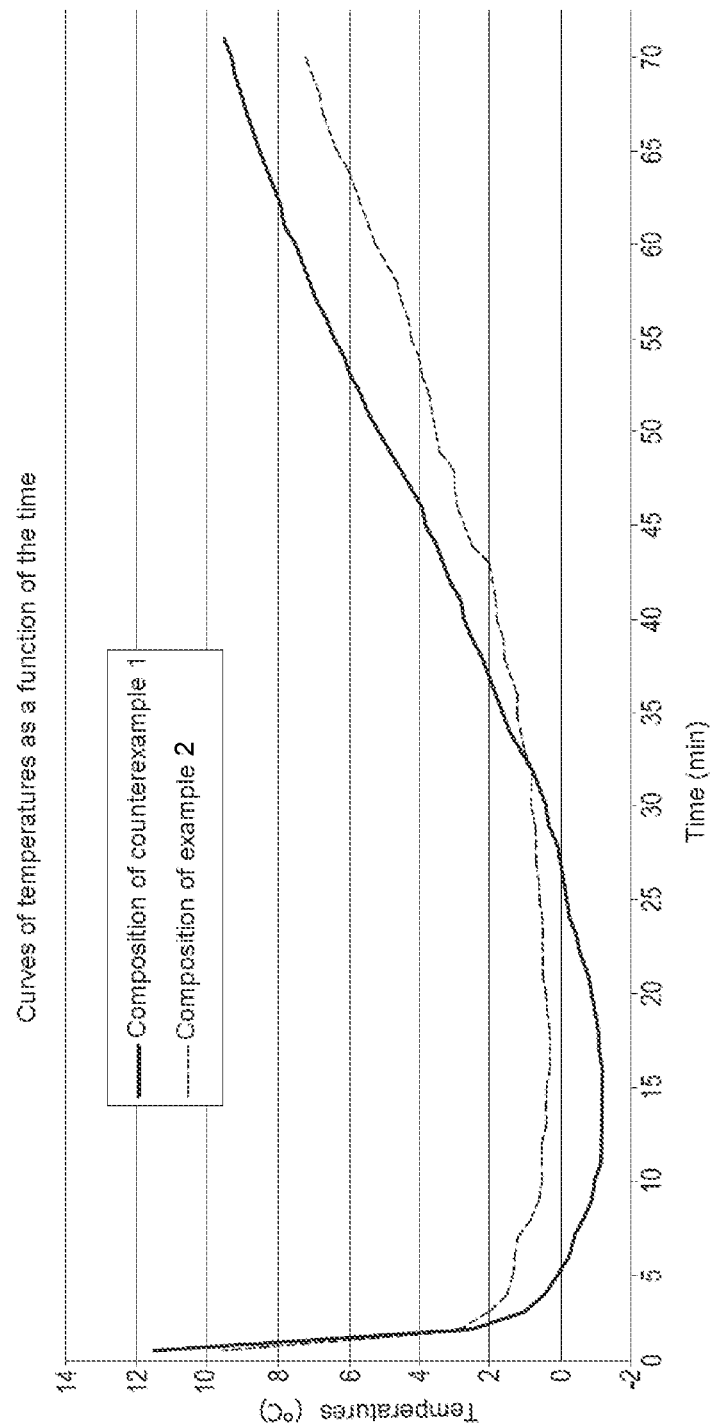

Apart from the preceding provisions, the invention also comprises other provisions which will emerge from the remainder of the description which follows, which relates to examples demonstrating the advantageous properties of the composition of the invention, and also to the graphs of the appended FIGS. 1 and 2 (FIGS. 1 and 2), which represent curves of temperatures as a function of the time which are obtained for the cryogenic compositions of example 1 and counterexample 1, and of example 2.

EXAMPLES

Example 1

A composition according to the invention is prepared by mixing 26.3 g of water with 2.24 g of dipropylene glycol (supplier: Interchimie), under manual stirring. 0.65 g of potassium polyacrylate beads having a diameter of 1.5 mm (Floragel hydrobeads, supplier: Axevi) are added to the water and dipropylene glycol mixture. The mixture is left standing at room temperature for 3 hours (step of hydration of the polymer beads), until the potassium polyacrylate beads have reached a mean diameter of 5.5 mm. 0.43 g of neopentylene glycol diheptanoate having a freezing point of −55° C. (DUB DPNG from Stéarinerie Dubois) is poured into a PVC bag of 5*7 cm with a thickness of 0.3 mm. The mixture, prepared beforehand, based on water, dipropylene glycol and potassium polyacrylate beads is also added to the PVC bag. The bag is subsequently sealed and placed in a freezer at −20° C. for 3 hours. During the freezing, a portion of the water present in the polymer beads changes phase and is converted into small ice crystals having the appearance of snow. Furthermore, the PVC bag remains flexible and conformable at the end of the freezing step.

The temperature of the sample is measured each minute for 70 minutes under a compression of 14 g·cm$^{-2}$, using a Testo 175 T2 temperature recorder, with a probe of NTC type. The measurements are carried out every minute at the interface between the frozen bag and a bag of water at 20° C. with a thickness of 2 cm. The curve of temperature as a function of time is represented in FIG. 1 (FIG. 1). The temperature of the bag always remains above 0° C. and stays below 5° C. for 61 minutes. The bag can thus be used for a cryotherapy treatment for 61 minutes.

The aging of the composition is also evaluated by measuring the number of freezing/thawing cycles. The aging becomes visible when the polymer beads begin to aggregate together, resulting in a decrease in the flexibility of the frozen bag. With the composition of the invention of example 1, the bag remains homogeneous and flexible up to the 25$^{th}$ freezing/thawing cycle.

Example 2

A composition according to the invention is prepared by mixing 1000 g of water with 10 g of butylene glycol, 10 g of pentylene glycol, 10 g of propylene glycol and 50 g of dipropylene glycol (supplier: Interchimie), under manual stirring. 25 g of potassium polyacrylate beads having a diameter of 3 mm (Floragel hydrobeads, supplier: Axevi) are added to the water, butylene glycol, pentylene glycol, propylene glycol and dipropylene glycol mixture. The mixture is left standing at room temperature for 3 hours (step of hydration of the polymer beads), until the potassium polyacrylate beads have reached a mean diameter of 8 mm. 5 g of isodecyl neopentanoate having a freezing point of −35° C. (DUB VCI 10 from Stéarinerie Dubois) is poured into a PVC bag of 5*7 cm with a thickness of 0.3 mm. The mixture, prepared beforehand, based on water, butylene glycol, pentylene glycol, propylene glycol, dipropylene glycol and potassium polyacrylate beads is also added to the PVC bag. The bag is subsequently sealed and placed in a freezer at −20° C. for 3 hours. During the freezing, a portion of the water present in the polymer beads changes phase and is converted into small ice crystals having the appearance of snow.

The temperature of the sample is measured each minute for 70 minutes under a compression of 14 g·cm$^{-2}$, using a Testo 175 T2 temperature recorder, with a probe of NTC type. The measurements are carried out every minute at the interface between the frozen bag and a bag of water at 20° C. with a thickness of 2 cm. The curve of temperature as a function of time is represented in FIG. 2 (FIG. 2). The temperature of the bag always remains above 0° C. and stays below 5° C. for 58 minutes. The bag can thus be used for a cryotherapy treatment for 58 minutes.

The aging of the composition is also evaluated by measuring the number of freezing/thawing cycles. The aging becomes visible when the polymer beads begin to aggregate together, resulting in a decrease in the flexibility of the frozen bag. With the composition of the invention of example 2, the bag remains homogeneous and flexible up to the 25$^{th}$ freezing/thawing cycle.

Counterexample 1

A composition according to example 1 of the patent EP 1 011 558 is prepared by mixing 27.75 g of water with 1.80 g of propylene glycol, under manual stirring. 0.45 g of Terra-Sorb acrylamide copolymer beads having a diameter of between 1 and 6 mm (supplier: Plant Health Care) are added to the water and propylene glycol mixture. The mixture is left standing at room temperature for 3 hours (step of hydration of the polymer beads), until the potassium polyacrylate beads have reached a mean diameter of 8 to 9 mm. The composition thus prepared is placed in a PVC bag of 5*7 cm with a thickness of 0.3 mm. The bag is subsequently sealed and placed in a freezer at −20° C. for 3 hours.

As for example 1, the temperature of the sample is measured each minute for 70 minutes under a compression of 14 g·cm$^{-2}$, using a Testo 175 T2 temperature recorder, with a probe of NTC type. The measurements are carried out every minute at the interface between the frozen bag and a bag of water at 20° C. with a thickness of 2 cm. The curve of temperature as a function of time is also represented in FIGS. 1 and 2 (FIGS. 1 and 2), for comparison with the compositions of the invention of examples 1 and 2. The temperature of the bag remains below 0° C. for approximately 25 minutes and then stays between 0° C. and 5° C. for 24 minutes. The bag can thus be used for a cryotherapy treatment for 24 minutes.

As for examples 1 and 2, the aging of the composition is evaluated by measuring the number of freezing/thawing cycles. From the 1$^{st}$ cycle, it is observed that the bag is less homogeneous and less flexible than the bags of examples 1 and 2. With the composition of the patent EP 1 011 558, the bag remains homogeneous and flexible up to the 10$^{th}$ freezing/thawing cycle. From the 11$^{th}$ cycle, aggregation of the polymer beads is observed.

Counterexample 2

A composition analogous to that of example 1 above is prepared but without neopentylene glycol diheptanoate (absence of hydrophobic compound in the composition).

The frozen bag obtained is less flexible than that of example 1 containing the hydrophobic compound.

As for example 1, the aging of the composition is evaluated by measuring the number of freezing/thawing cycles. In the absence of hydrophobic compound, the composition exhibits premature aging from the 15$^{th}$ freezing/thawing cycle.

Counterexample 3

A composition according to the invention is prepared as described in example 1 by replacing the neopentylene glycol diheptanoate having a freezing point of −55° C. (DUB DPNG from Stéarinerie Dubois) with liquid petrolatum having a freezing point of −10° C. (Huile de Vaseline Codex 22 from Interchimie). The mixture thus prepared is added to the PVC bag. The bag is subsequently sealed and placed in a freezer at −20° C. for 3 hours. During freezing, the PVC bag becomes rigid: negative interactions between the liquid petrolatum and the PVC bag are observed. The bag is not sufficiently flexible to be able to be used as flexible medical bag.

The invention claimed is:

1. A cryogenic composition, comprising a hydrophobic compound in liquid form in which granules of superabsorbent polymer charged with water and with humectant are immersed, said hydrophobic compound having a freezing point of less than 0°, and wherein said hydrophobic compound is chosen from neopentylene glycol diheptanoate, isopropyl sebacate, isodecyl neopentanoate, isostearyl isostearate, and their mixtures.

2. The cryogenic composition as claimed in claim 1, which comprises:
   (a) from 0.2% to 3% by weight of the hydrophobic compound,
   (b) from 1% to 6% by weight of superabsorbent polymer granules,
   (c) from 75% to 95% by weight of water,
   (d) from 6% to 10% by weight of a humectant,
   said percentages being expressed as percentages by weight with respect to the total weight of the composition, and the total weight of the composition representing 100%.

3. The cryogenic composition as claimed in claim 1, wherein the superabsorbent polymer is chosen from crosslinked sodium or potassium polyacrylates, polyacrylamides, copolymers based on ethylene and maleic anhydride, vinyl alcohol copolymers, crosslinked polyethylene oxide, polymers based on starch, on gum and on cellulose derivatives, pectins, alginates, agar (or agarose), polyethyleneamines, polyvinylamines and their mixtures.

4. The cryogenic composition as claimed in claim 1, wherein said granules of superabsorbent polymer are provided in the form of spherical particles having a diameter of 1 to 6 mm when they are dehydrated, said spherical particles being able to absorb at least 40 times their weight.

5. The cryogenic composition as claimed in claim 4, wherein said spherical particles of superabsorbent polymer are sodium or potassium polyacrylate beads, having a diameter of 1 to 3 mm when they are dehydrated.

6. The cryogenic composition as claimed in claim 1, wherein the humectant is chosen from glycerol, sorbitol, polyethylene glycol, (di)propylene glycol, polypropylene glycol, 1,5-pentanediol, propylene glycol, butylene glycol, diethylene glycol, liquid paraffin and their mixtures.

7. The cryogenic composition as claimed in claim 6, wherein the humectant is dipropylene glycol.

8. The cryogenic composition as claimed in claim 1, which comprises:
   (a) from 0.2% to 2% by weight of the hydrophobic compound,
   (b) from 1.5% to 3% by weight of superabsorbent polymer granules,
   (c) from 85% to 90% by weight of water,
   (d) from 7% to 9% by weight of a humectant,
   said percentages being expressed as percentages by weight with respect to the total weight of the composition, and the total weight of the composition representing 100%.

9. A process for the preparation of a cryogenic composition as claimed in claim 1, comprising the following steps:
   (i) mixing the water and the humectant, under stirring,
   (ii) adding the granules of superabsorbent polymer to the mixture obtained at the end of step (i), under stirring,
   (iii) maturing the granules of superabsorbent polymer present within the mixture obtained at the end of step (ii), by allowing said mixture to stand at room temperature, preferably until the granules of superabsorbent polymer have reached a size of between two and four times their initial size, and
   (iv) incorporating the mixture obtained at the end of step (iii) in a container comprising the hydrophobic compound in the liquid form, under stirring.

10. The process as claimed in claim 9, wherein step (iii) of maturing the granules of superabsorbent polymer is carried out over a period of time ranging from 1 to 5 hours, and preferably over a period of time ranging from 2 to 4 hours.

11. A thermal treatment device, comprising a leaktight container, within which is contained a cryogenic composition as defined in claim 1.

12. The device as claimed in claim 11, wherein said container is a leaktight and flexible medical bag made of a material chosen from polyvinyl chloride (PVC), polychloroprene (neoprene), polytetrafluoroethylene (PTFE) or polyethylene (PE).

13. A medical device chosen from a face mask, a splint for the shoulder, elbow, ankle, knee, hip or wrist, and any support comprising a leaktight and flexible medical bag as defined in claim 12.

14. A method of use of a cryogenic composition as defined according to claim 1, the method comprising lowering or maintaining the temperature of foodstuffs, promoting preservation of the foodstuffs, or in transportation of heat-sensitive articles in a cold environment, with the cryogenic composition acting as a cooling member.

* * * * *